United States Patent
Shao-Horn et al.

(10) Patent No.: US 11,492,329 B2
(45) Date of Patent: Nov. 8, 2022

(54) SMALL MOLECULE AND POLYMERIC ANIONS FOR LITHIUM-SOLVATE COMPLEXES: SYNTHESIS AND BATTERY APPLICATIONS

(71) Applicant: MASSACHUSETTS INSTITUTE OF TECHNOLOGY, Cambridge, MA (US)

(72) Inventors: Yang Shao-Horn, Newton, MA (US); Jeremiah Johnson, Boston, MA (US); Wenxu Zhang, Belmont, MA (US); Mingjun Huang, Everett, MA (US); Shuting Feng, Cambridge, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 0 days.

(21) Appl. No.: 16/835,137

(22) Filed: Mar. 30, 2020

(65) Prior Publication Data

US 2020/0308107 A1  Oct. 1, 2020

Related U.S. Application Data

(60) Provisional application No. 62/827,158, filed on Mar. 31, 2019.

(51) Int. Cl.
| | |
|---|---|
| *C07C 311/15* | (2006.01) |
| *H01M 10/0525* | (2010.01) |
| *C08L 23/32* | (2006.01) |
| *H01M 10/0569* | (2010.01) |
| *H01M 10/0568* | (2010.01) |

(52) U.S. Cl.
CPC ......... *C07C 311/15* (2013.01); *C08L 23/32* (2013.01); *H01M 10/0525* (2013.01); *H01M 10/0568* (2013.01); *H01M 10/0569* (2013.01)

(58) Field of Classification Search
CPC ............... C07C 311/15; C07C 311/48; H01M 10/0525; H01M 10/0569; H01M 10/0568; H01M 2300/0045; C08L 23/32; Y02E 60/10

See application file for complete search history.

(56) References Cited

U.S. PATENT DOCUMENTS

| | | | |
|---|---|---|---|
| 2018/0145370 A1* | 5/2018 | Buisine | H01G 11/56 |
| 2018/0208712 A1* | 7/2018 | Johnson | H01M 8/1027 |
| 2018/0212275 A1* | 7/2018 | Johnson | H01M 10/0565 |

* cited by examiner

*Primary Examiner* — Andrew J. Oyer
(74) *Attorney, Agent, or Firm* — Honigman LLP

(57) ABSTRACT

Electrolytes and polymers for a lithium battery can include a fluorinated aryl sulfonimide salt or fluorinated aryl sulfonimide polymer.

19 Claims, 14 Drawing Sheets

SMALL MOLECULE AND POLYMERIC ANIONS FOR LITHIUM-SOLVATE COMPLEXES: SYNTHESIS AND BATTERY APPLICATIONS

CLAIM OF PRIORITY

This application claims priority to U.S. Provisional Patent Application No. 62/827,158, filed Mar. 31, 2019, which is incorporated by reference in its entirety.

STATEMENT OF FEDERAL SUPPORT

This invention was made with Government support under Grant No. CHE-1351646 awarded by the National Science Foundation (NSF). The Government has certain rights in the invention.

TECHNICAL FIELD

The invention relates to solvate ionic liquids.

BACKGROUND

Lithium-ion batteries have attracted considerable attention as one of the most promising electrical energy storage (EES) systems. This class of batteries is currently the cornerstone of the modern portable electronics industry and are at the forefront of potential technologies to replace gasoline in vehicles and reduce society's dependence on fossil fuels. The organic liquid electrolytes employed by commercial Lithium-ion batteries, however, pose significant technical challenges for the successful implementation and continued development of this technology in demanding applications, particularly electric vehicles. Conventional carbonate-based solvent (in both liquid and vapor form) can be readily ignited by internal/external short circuits, resulting in the possibility of explosive accidents, which, in selected cases, have resulted in considerable property damage and injuries to individuals. Room-temperature Ionic liquids (IL) have been identified as desirable alternatives to organic-solvent-based electrolytes, due to their wide electrochemical stability window, high ionic conductivity, negligible vapor pressure (resulting in poor flammability), and high thermal stability.

SUMMARY

In general, a compound can be a fluorinated aryl sulfonimide salt or fluorinated aryl sulfonimide polymer. The compound can be an electrolyte and or polymer for a battery.

In one aspect, a compound can have a formula I:

$$R_1-\underset{\underset{O}{\|}}{\overset{\overset{O}{\|}}{S}}-\underset{}{\overset{M}{N}}-\underset{\underset{O}{\|}}{\overset{\overset{O}{\|}}{S}}-R_2 \quad (I)$$

M can be a metal cation.

$R_1$ can be alkyl, alkenyl, alkynyl, aryl, heteroaryl, or alkoxy.

$R_2$ can be alkyl, alkenyl, alkynyl, aryl, heteroaryl, or alkoxy.

In the compound of formula I, at least one of $R_1$ and $R_2$ is substituted and includes at least one fluorine.

In certain circumstances, M can be a lithium ion, a sodium ion, or a potassium ion.

In certain circumstances, $R_1$ can be a fluorinated C1-C6 alkyl.

In certain circumstances, $R_2$ can be a fluorinated aryl.

In certain circumstances, $R_2$ can be a fluorinated aryl optionally substituted with one or more amino group, alkoxy group or alkylthio group.

In certain circumstances, the compound can have the formula:

$$F_3C-\underset{\underset{O}{\|}}{\overset{\overset{O}{\|}}{S}}-\underset{}{\overset{Li}{N}}-\underset{\underset{O}{\|}}{\overset{\overset{O}{\|}}{S}}-\underset{F\ F}{\overset{F\ F}{\bigcirc}}-Q$$

wherein Q is a fluoro, an alkoxy group or alkylthio group.

In certain circumstances, Q can be fluoro, C1-C4 alkylthio, C1-C4 alkoxy, or a polyolefin including a thio or oxy moiety.

In certain circumstances, the compound can be:

$$F_3C-\underset{\underset{O}{\|}}{\overset{\overset{O}{\|}}{S}}-\underset{}{\overset{Li}{N}}-\underset{\underset{O}{\|}}{\overset{\overset{O}{\|}}{S}}-\underset{F\ F}{\overset{F\ F}{\bigcirc}}-S-\overset{}{\underset{}{<}} \quad \text{or}$$

$$F_3C-\underset{\underset{O}{\|}}{\overset{\overset{O}{\|}}{S}}-\underset{}{\overset{Li}{N}}-\underset{\underset{O}{\|}}{\overset{\overset{O}{\|}}{S}}-\underset{F\ F}{\overset{F\ F}{\bigcirc}}-F.$$

In another aspect, a compound can include a polyolefin including a thio or oxy moiety and having a structure of formula II or formula III $$\left(\begin{array}{c}\\ \\ \underset{Z}{|}\end{array}\right)_m\left(\begin{array}{c}\\ \\ \end{array}\right)_n \quad (II)$$

$$\left(\begin{array}{c}\\ \\ \underset{Z}{|}\end{array}\right)_m\left(\begin{array}{c}\\ \\ \end{array}\right)_n \quad (III)$$

n can be 1-10,000.

Each m can be 0, 1, 2, or 3.

Z can be $$R_1-\underset{\underset{O}{\|}}{\overset{\overset{O}{\|}}{S}}-\underset{}{\overset{M}{N}}-\underset{\underset{O}{\|}}{\overset{\overset{O}{\|}}{S}}-R_3-L-\xi,$$

in which M can be a metal cation, $R_1$ can be alkyl, alkenyl, alkynyl, aryl, heteroaryl, and alkoxy, $R_3$ can be alkylene, alkenylene, alkynylene, arylene, heteroarylene, and alkyleneoxy, and L can be O or S; and wherein at least one of $R_1$ and $R_2$ is substituted and includes at least one fluorine.

In certain circumstances, the polyolefin can have a structure of formula (IV) or (V):

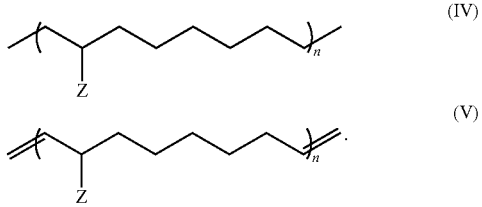

In certain circumstances, M can be a lithium ion, a sodium ion, or a potassium ion.

In certain circumstances, $R_1$ can be a fluorinated C1-C6 alkyl.

In certain circumstances, $R_3$ can be a fluorinated arylene.

In certain circumstances, $R_3$ can be a fluorinated arylene optionally substituted with one or more amino group, alkoxy group or alkylthio group.

In certain circumstances, $R_1$ can be trifluoromethyl and $R_3$ can be fluorinated phenylene.

In certain circumstances, wherein the compound can be:

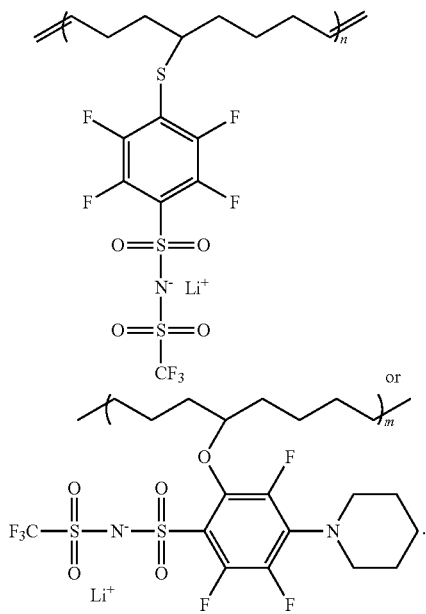

In another aspect, a battery can include a compound described herein.

Other features, objects, and advantages will be apparent from the description, drawings, and claims.

DETAILED DESCRIPTION

Figure 1:
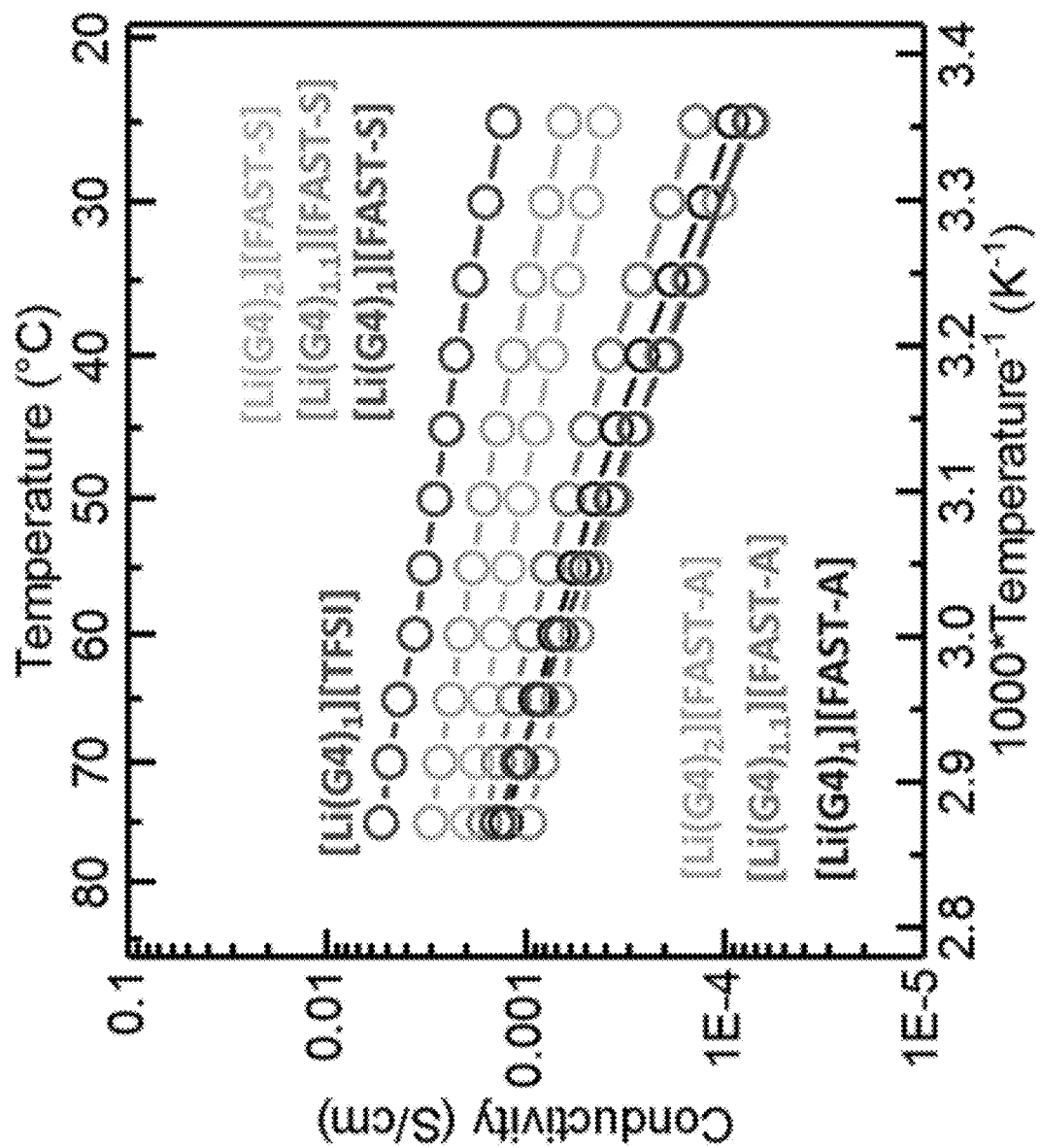
FIGS. 1-9 feature two novel SILs based on perfluoroaryl sulfonimide Li salts.
Figure 2:
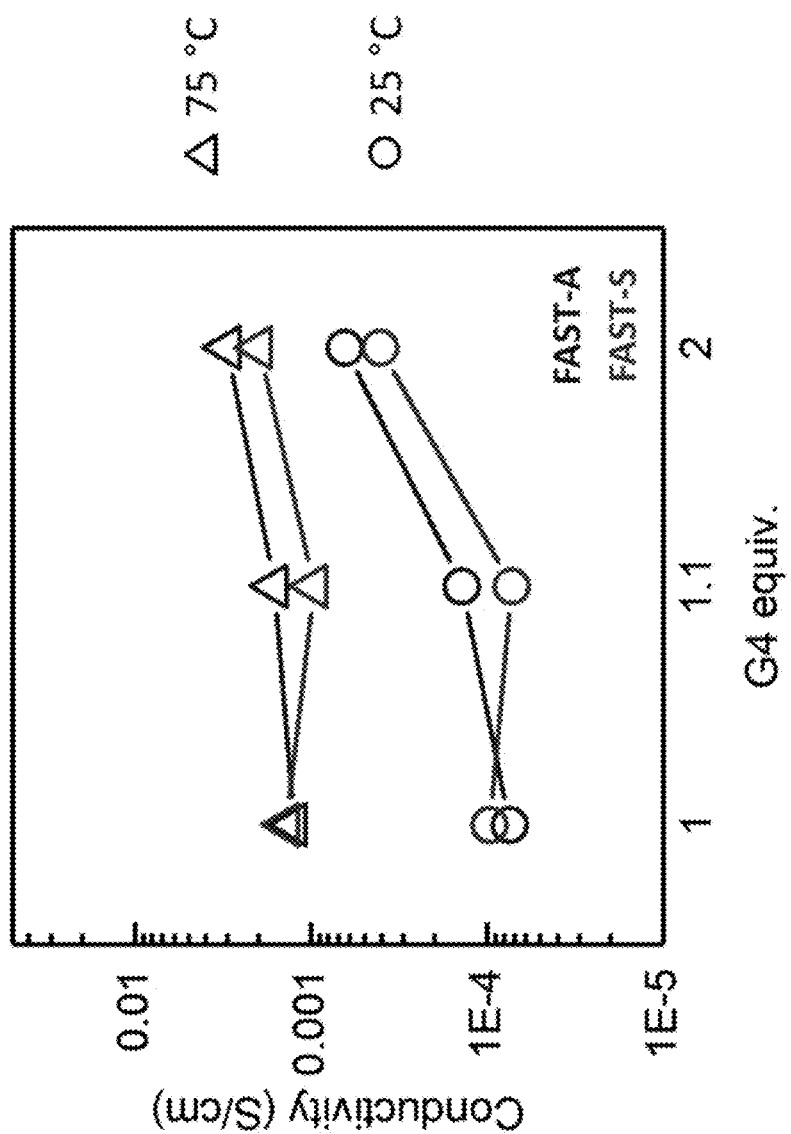
Figure 3:
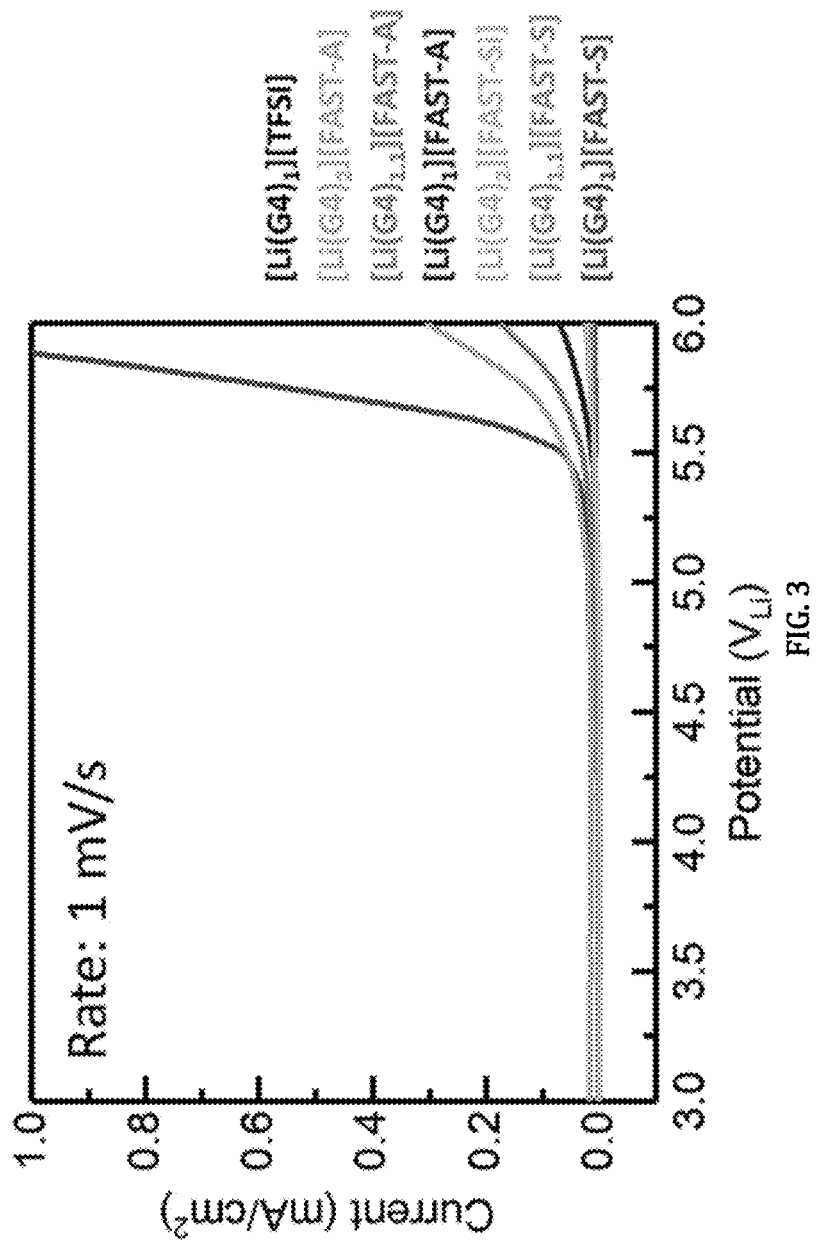

Solvate Ionic Liquids (SILs) are unique and rare entities that form when a highly dissociative metal (e.g., Li+) salt is mixed with a strongly coordinating solvent (e.g., glyme) to form a liquid. The properties of SILs are completely different than those of their constituent salt and solvent; a true SIL is better described as novel salt with a supramolecular solvent-coordinated cation. Notably, most 1:1 salt+solvent mixtures are solids or the solvent does not completely solvate every salt molecule; such mixtures are not SILs.

To date, the most studied SIL is formed from a 1:1 mixture of the salt LiTFSI and tetraglyme (G4). In this supramolecular liquid, each molecule of G4 coordinates to one Li+ cation forming a liquid that behaves nothing like G4 or LiTFSI. For example, the LiTFSI:G4 SIL has stability up to ~5 V whereas G4 is reported to be unstable at ~4.5 V. This difference is due to the interaction of G4 oxygen atoms with the Li+ ion making it effectively a new cation, and that fact that there is negligible "free" or unbound G4 in the system.

To date, there are a very small number of reported SILs. In order to leverage the unique properties of these supramolecular compounds, new SILs are needed. In addition, since SILs are, by definition, liquids, ways to provide them with improved mechanical robustness are needed.

In general, a compound can be a fluorinated aryl sulfonimide salt or fluorinated aryl sulfonimide polymer. The compound can be an electrolyte and or polymer for a battery. The electrolyte can be a mixture including a lithium bis(trifluoromethanesulfonyl)imide (LiTFSI).

The compound can have a formula I:

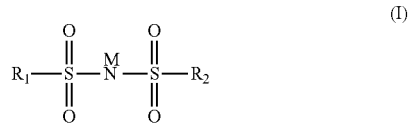

M can be a metal cation.

$R_1$ can be alkyl, alkenyl, alkynyl, aryl, heteroaryl, or alkoxy.

$R_2$ can be alkyl, alkenyl, alkynyl, aryl, heteroaryl, or alkoxy.

In the compound of formula I, at least one of $R_1$ and $R_2$ is substituted and includes at least one fluorine.

In certain circumstances, M can be a lithium ion, a sodium ion, or a potassium ion.

In certain circumstances, $R_1$ can be a fluorinated C1-C6 alkyl.

In certain circumstances, $R_2$ can be a fluorinated aryl.

In certain circumstances, $R_2$ can be a fluorinated aryl optionally substituted with one or more amino group, alkoxy group or alkylthio group.

In certain circumstances, the compound can have the formula:

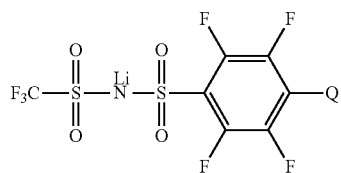

wherein Q is a fluoro, an alkoxy group or alkylthio group.
In certain circumstances, Q can be fluoro, C1-C4 alkylthio, C1-C4 alkoxy, or a polyolefin including a thio or oxy moiety.

In certain circumstances, the compound can be:

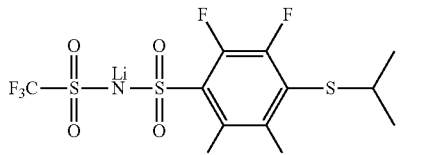

or

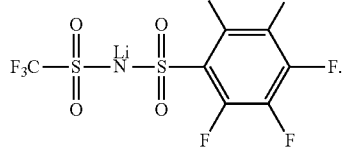

The compound also can include a polyolefin including a thio or oxy moiety and having a structure of formula II or formula III

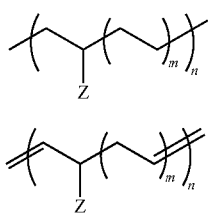

n can be 1-10,000.
Each m can be 0, 1, 2, or 3.
Z can be

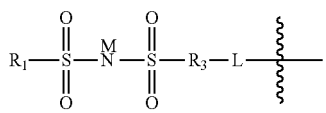

in which M can be a metal cation, $R_1$ can be alkyl, alkenyl, alkynyl, aryl, heteroaryl, and alkoxy, $R_3$ can be alkylene, alkenylene, alkynylene, arylene, heteroarylene, and alkyleneoxy, and L can be O or S; and wherein at least one of $R_1$ and $R_2$ is substituted and includes at least one fluorine.

In certain circumstances, the polyolefin can have a structure of formula (IV) or (V):

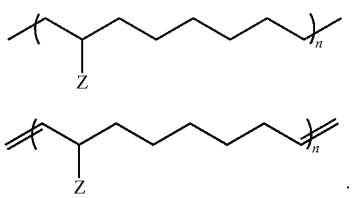

In certain circumstances, M can be a lithium ion, a sodium ion, or a potassium ion.

In certain circumstances, $R_1$ can be a fluorinated C1-C6 alkyl.

In certain circumstances, $R_3$ can be a fluorinated arylene.
In certain circumstances, $R_3$ can be a fluorinated arylene optionally substituted with one or more amino group, alkoxy group or alkylthio group.

In certain circumstances, $R_1$ can be trifluoromethyl and $R_3$ can be fluorinated phenylene.

In certain circumstances, wherein the compound can be:

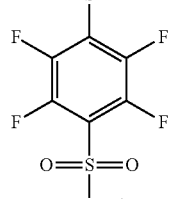

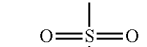

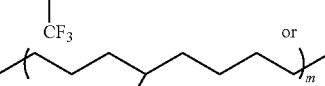

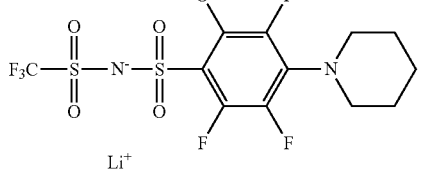

In another aspect, a battery can include a compound described herein.

"Alkyl" refers to a group of 1-18, 1-16, 1-12, 1-10, preferably 1-8, more preferably 1-6 unsubstituted or substituted hydrogen-saturated carbons connected in linear, branched, or cyclic fashion, including the combination in linear, branched, and cyclic connectivity. Non-limiting examples include methyl, ethyl, propyl, isopropyl, butyl, and pentyl.

"Alkenyl" refers to a group of unsubstituted or substituted hydrocarbons containing 2-18, 2-16, 2-12, 2-10, preferably 2-8, more preferably 2-6 carbons, which are linear, branched, cyclic, or in combination thereof, with at least one carbon-to-carbon double bond.

"Alkynyl" refers to a group of unsubstituted or substituted hydrocarbons containing 2-18, 2-16, 2-12, 2-10, preferably 2-8, more preferably 2-6 carbons, which are linear, branched, cyclic, or in combination thereof, with at least one carbon-to-carbon triple bond.

"Aryl" refers to a $C_6$-$C_{14}$ aromatic hydrocarbon. For example, aryl can be phenyl, napthyl, or fluorenyl.

"Heteroaryl" refers to a $C_6$-$C_{14}$ aromatic hydrocarbon having one or more heteroatoms, such as N, O or S. The heteroaryl can be substituted or unsubstituted. Examples of a heteroaryl include, but are not limited to, azaindole, azepinyl, acridinyl, benzimidazolyl, benzindolyl, 1,3-benzodioxolyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzofurazanyl, benzothiazolyl, benzothienyl, benzothieno[3,2-d]pyrimidinyl, benzotriazolyl, benzo[4,6]imidazo[1,2a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). In some embodiments, the heteroaryl can be dithiazinyl, furyl, imidazolyl, azaindolyl, indolyl, isoquinolinyl, isoxazolyl, oxadiazolyl (e.g., (1,3,4)-oxadiazolyl, (1,2,3)-oxadiazolyl, or (1,2,4)-oxadiazolyl), oxazolyl, pyrazinyl, pyrazolyl, pyrazyl, pyridazinyl, pyridinyl, pyrimidinyl, pyrimidyl, pyrrolyl, quinolinyl, tetrazolyl, thiazolyl, thienyl, triazinyl, (1,2,3)-triazolyl, or (1,2,4)-triazolyl. The substituent on the heteroaryl group can be amino, alkylamino, or methyleneamino.

FIGS. 1-9 feature two novel SILs based on perfluoroaryl sulfonimide Li salts.

Figure 10:
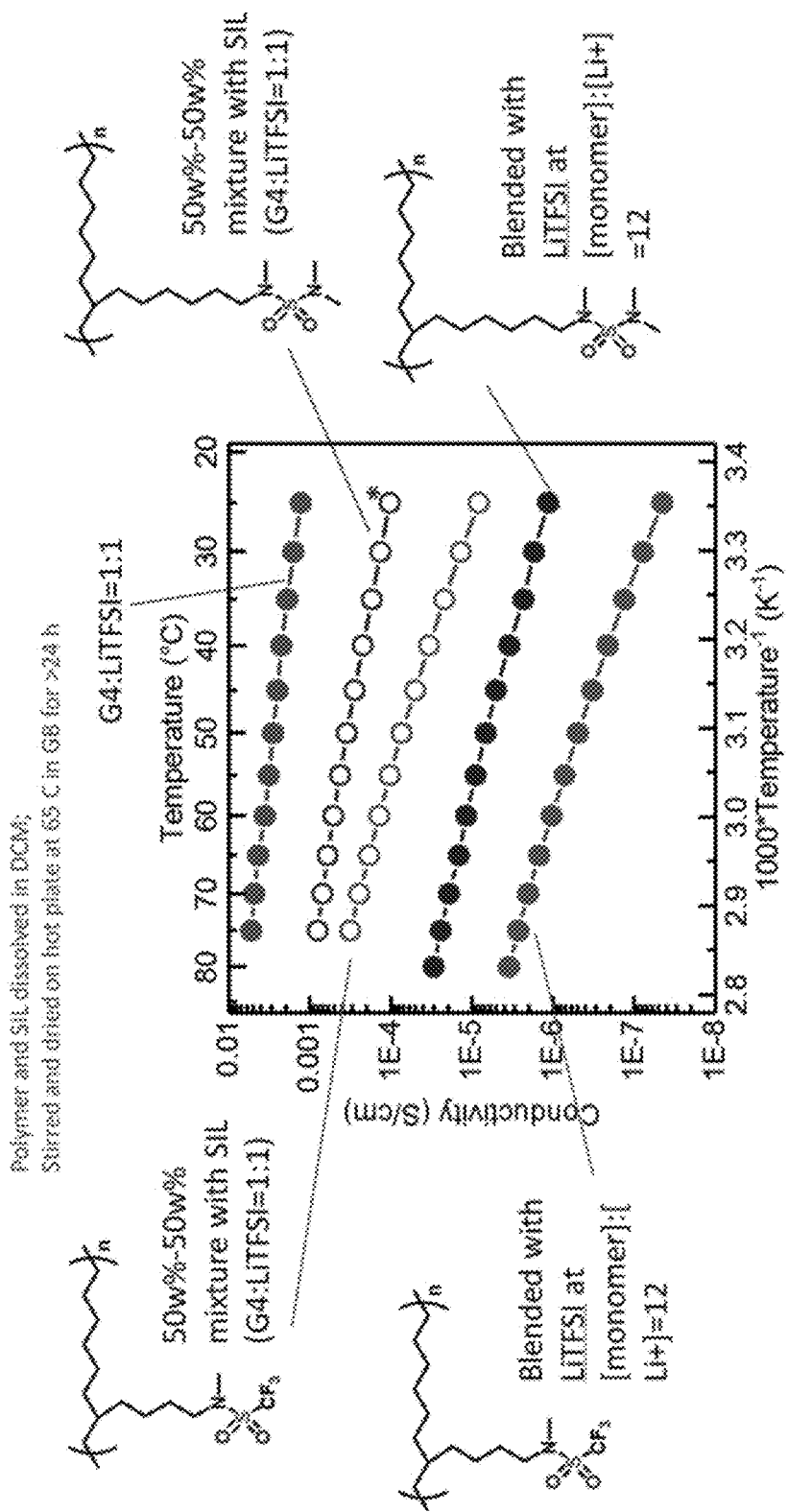
FIGS. 10-12 feature novel polymer+SIL composite materials that are not fluids yet display outstanding electrochemical stability (>5 V), good room temperature ionic conductivity (>$10^{-4}$ S/cm).
Figure 11:
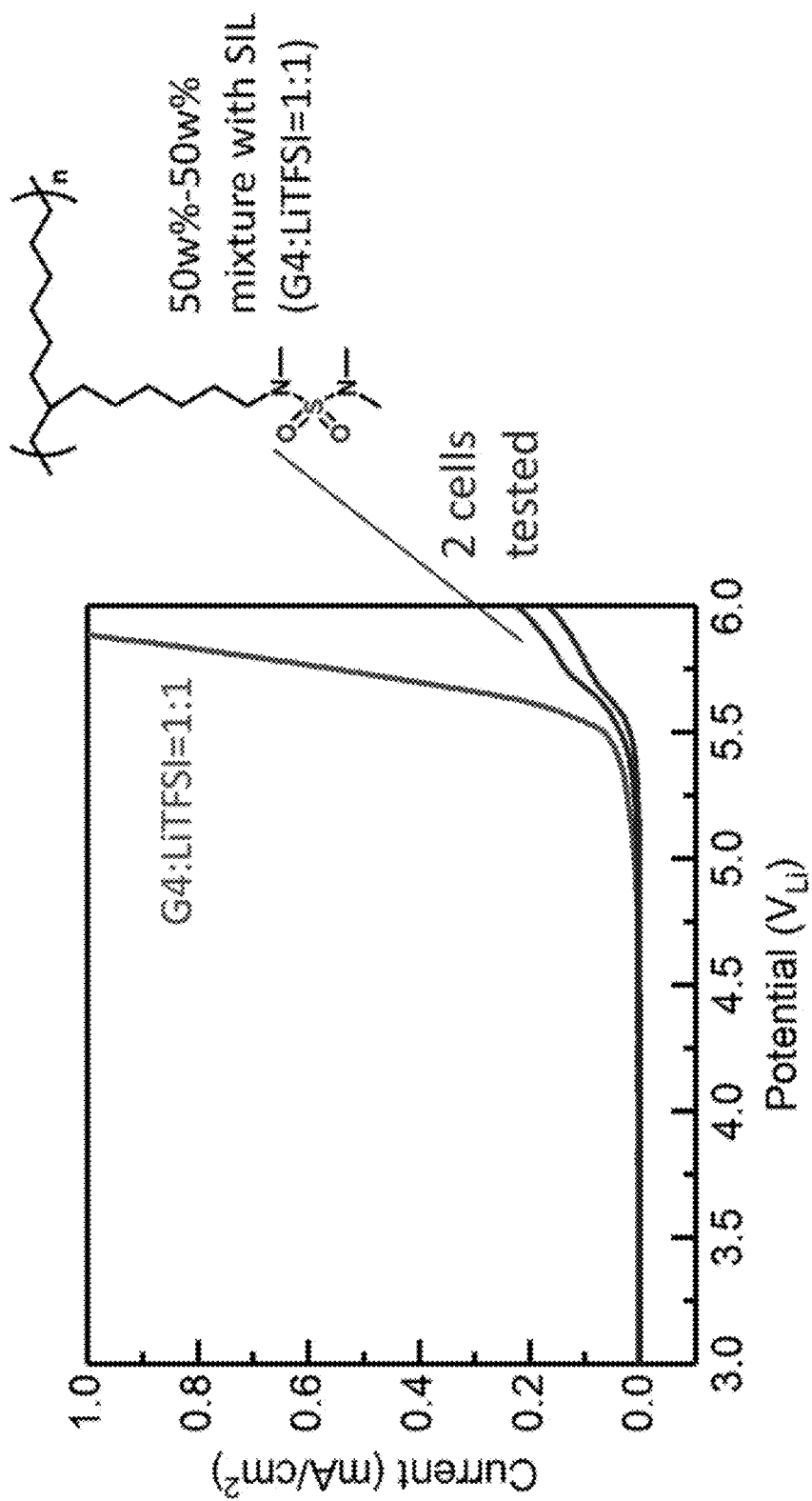
Figure 12:
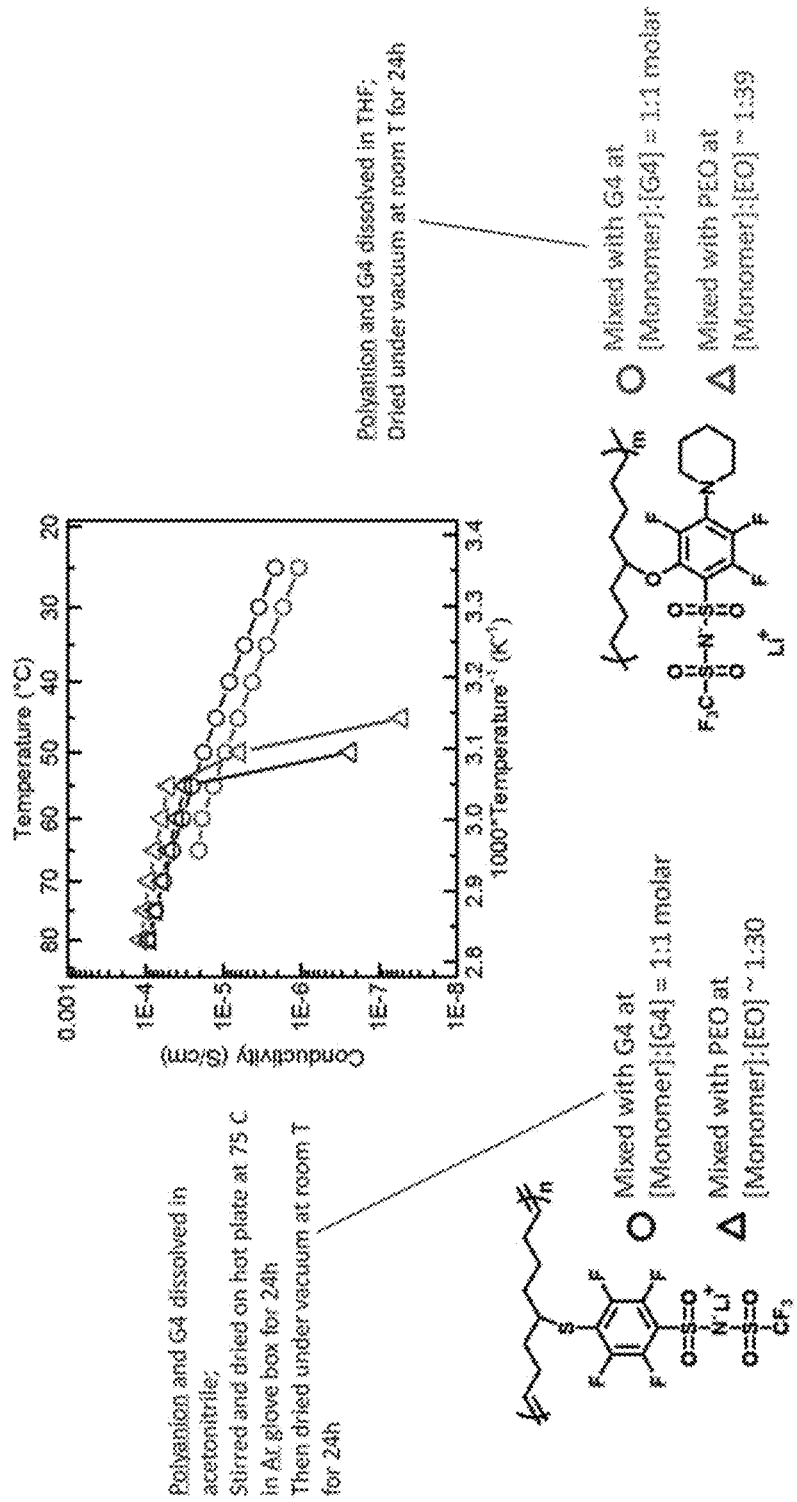

FIGS. 10-12 feature novel polymer+SIL composite materials that are not fluids yet display outstanding electrochemical stability (>5 V), good room temperature ionic conductivity (>10$^{-4}$ S/cm).

Two Novel FAST SILs have been identified. Fluorinated Aryl Sulfonimide Tagged (FAST) salts are highly dissociative. FASTs can form SILs when mixed with G4. Indeed, our first tests using FAST-A and FAST-S (shown below) indicate that they do indeed for novel SILs (called "[Li(G4)$_1$][FAST-S]" and "[Li(G4)$_1$][FAST-A]" below.

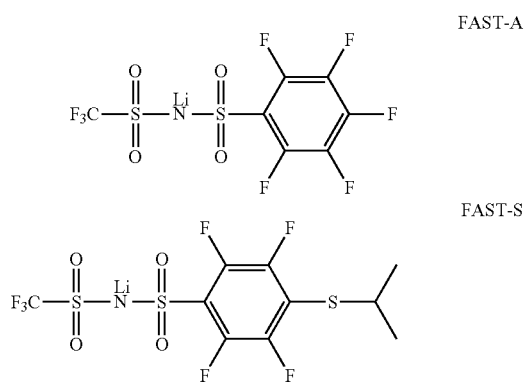

The FAST SILs display ~10× lower ionic conductivity than LiTFSI SIL likely due to high viscosity. Nevertheless, the conductivities are very promising. The electrochemical oxidative stability of G4-based SIL electrolytes show they can be used in a battery. The FAST-SILs display much greater electrochemical stability than the common LiTFSI SIL. Strikingly, the [Li(G4)$_1$][FAST-S] SIL is stable up to ~6 V.

Figure 4A:
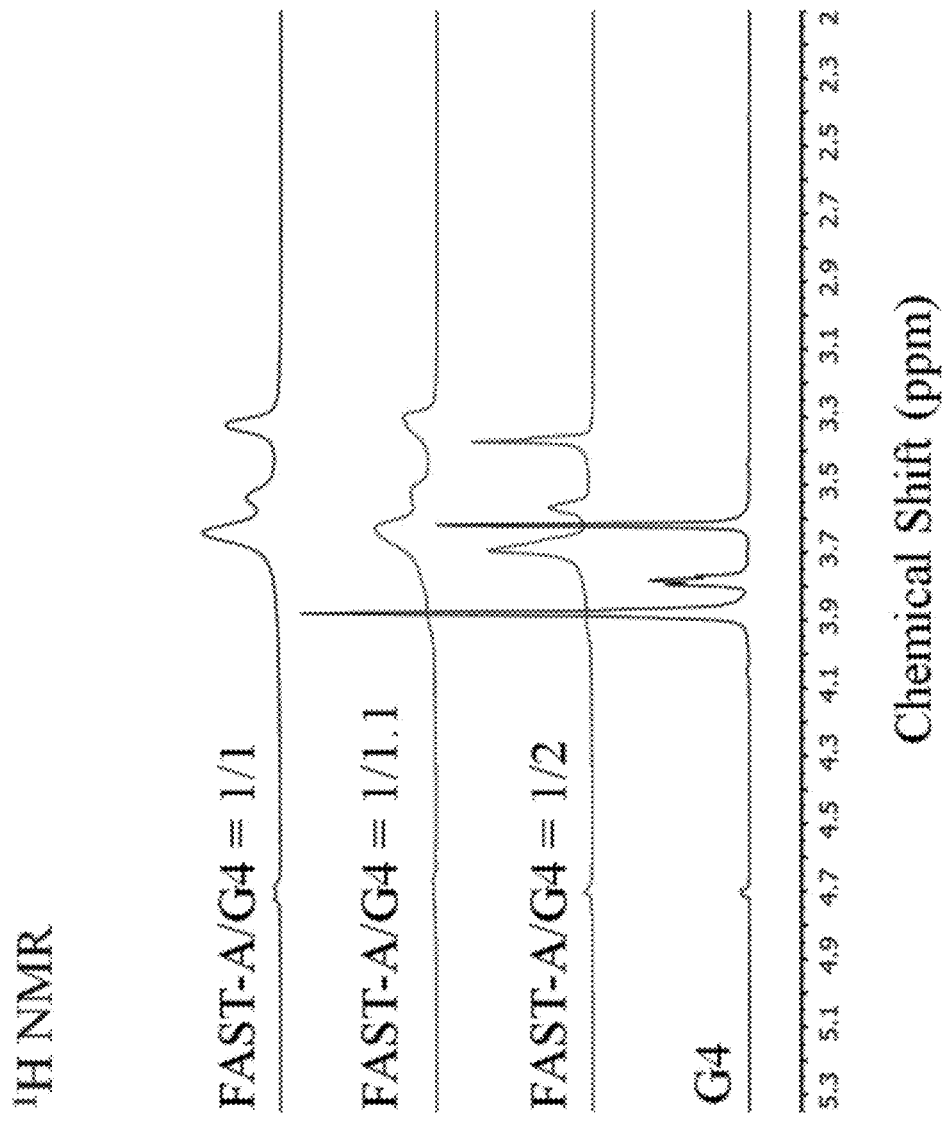
Figure 4B:
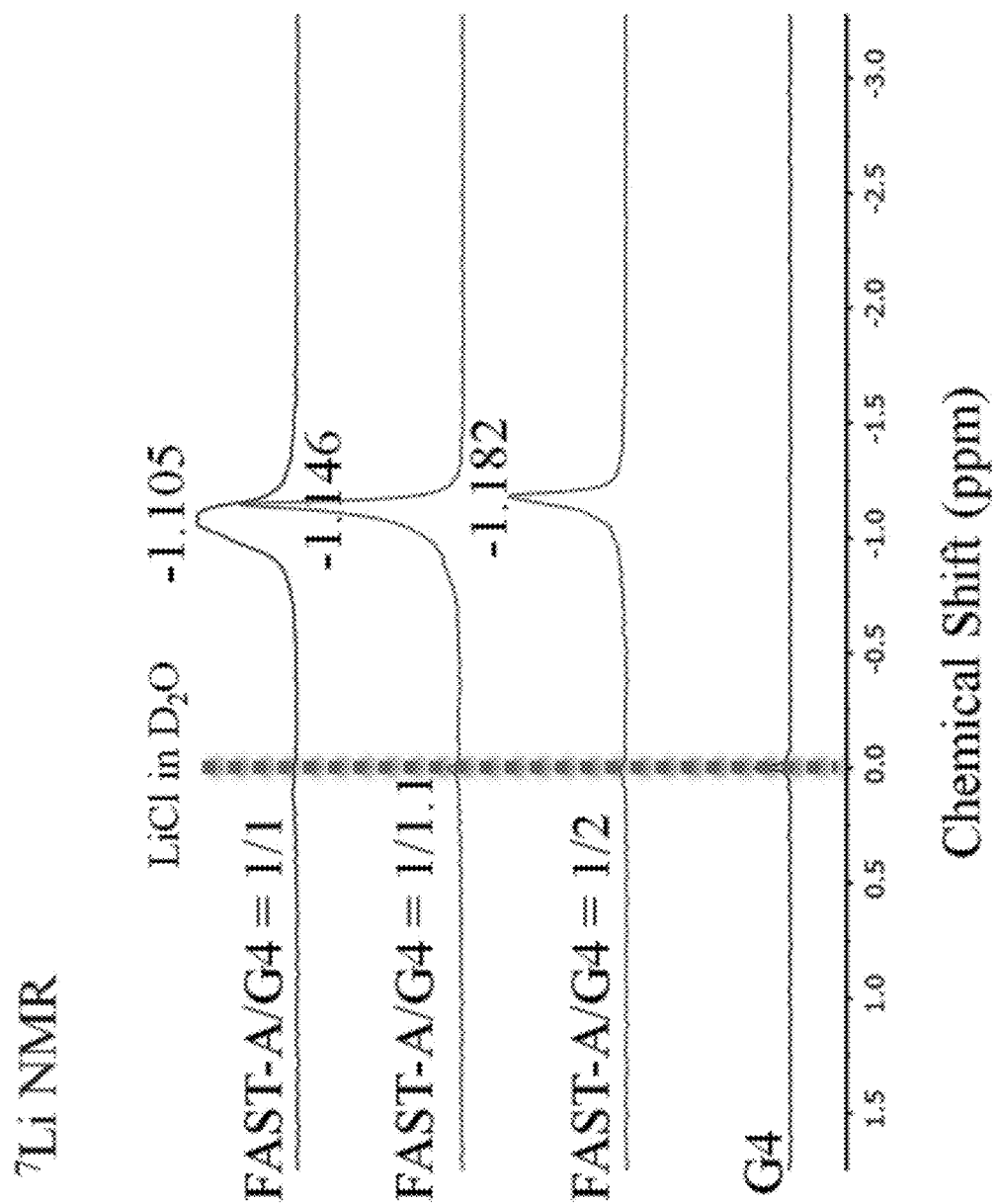

FIGS. 4A and 4B depict $^1$H and $^7$Li NMR spectroscopy of FAST-A SIL. The NMR data confirm that there is very little free G4 in these systems, and the SILs are highly dissociated.

Figure 5A:
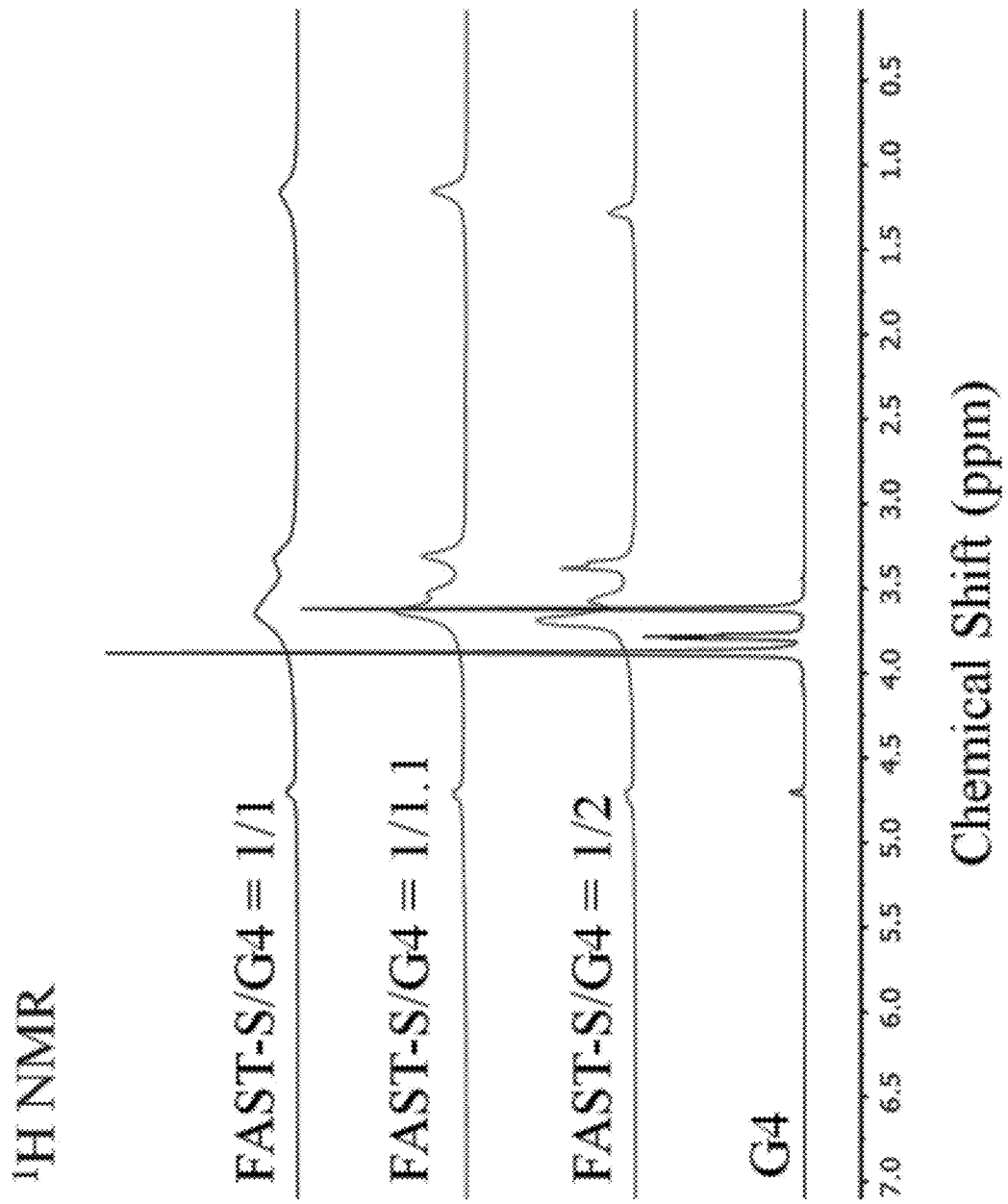
Figure 5B:
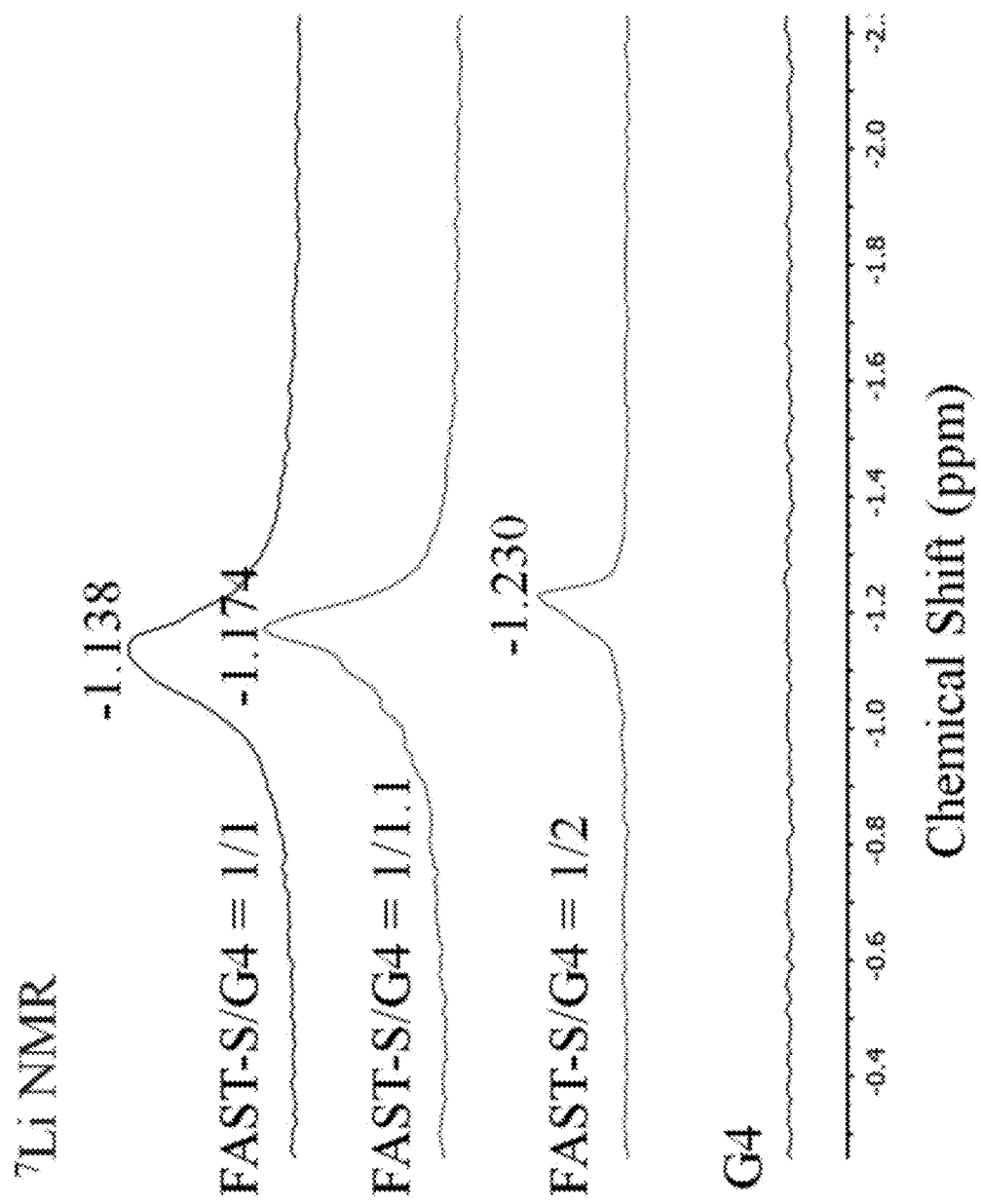

FIGS. 5A and 5B depict $^1$H and $^7$Li NMR spectroscopy of FAST-S SIL. The NMR data confirm that there is very little free G4 in these systems, and the SILs are highly dissociated.

Figure 6:
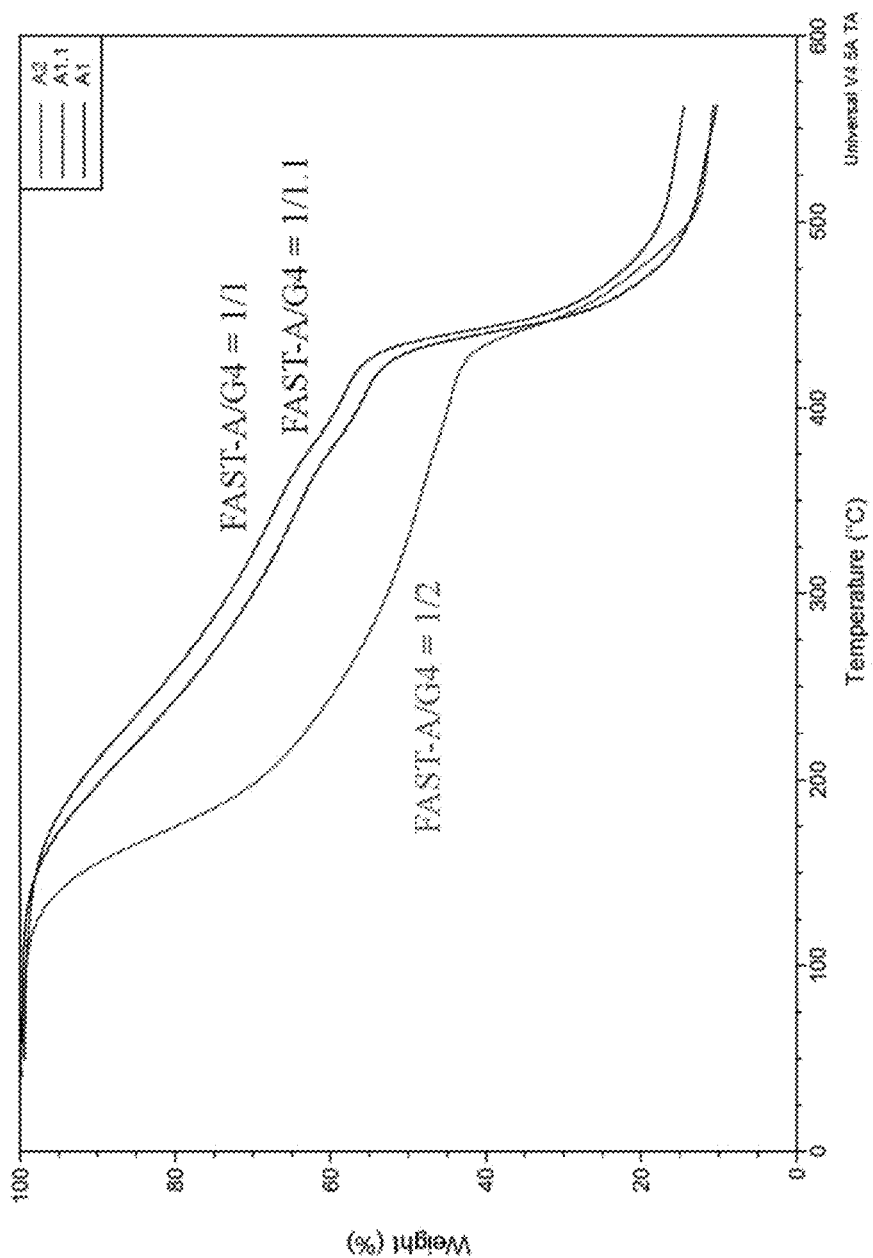

FIG. 6 depicts thermal gravimetric analysis showing improved thermal stability of 1:1 SIL (TGA rate: 20° C./min).

Figure 7:
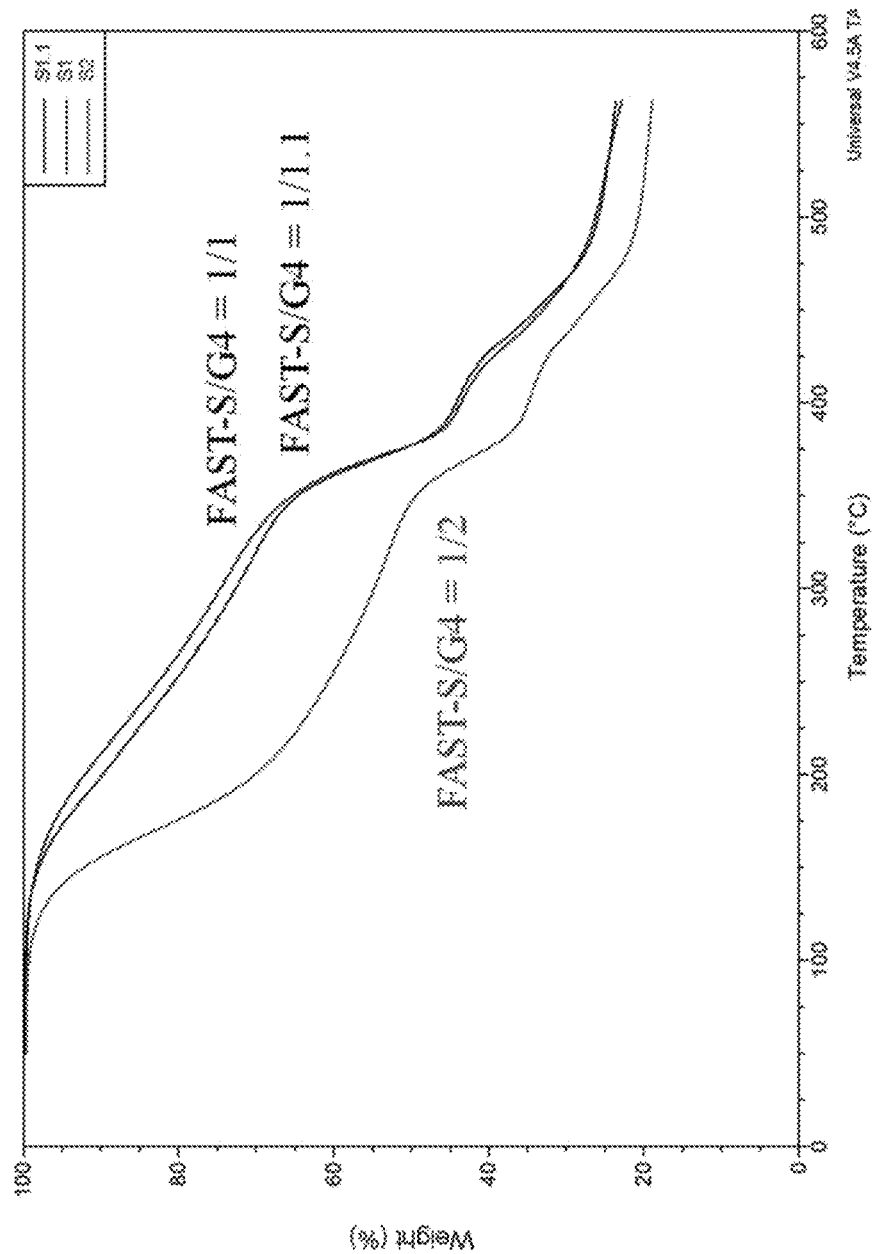

FIG. 7 depicts thermal gravimetric analysis showing improved thermal stability of 1:1 SIL (TGA rate: 20° C./m).

Figure 8:
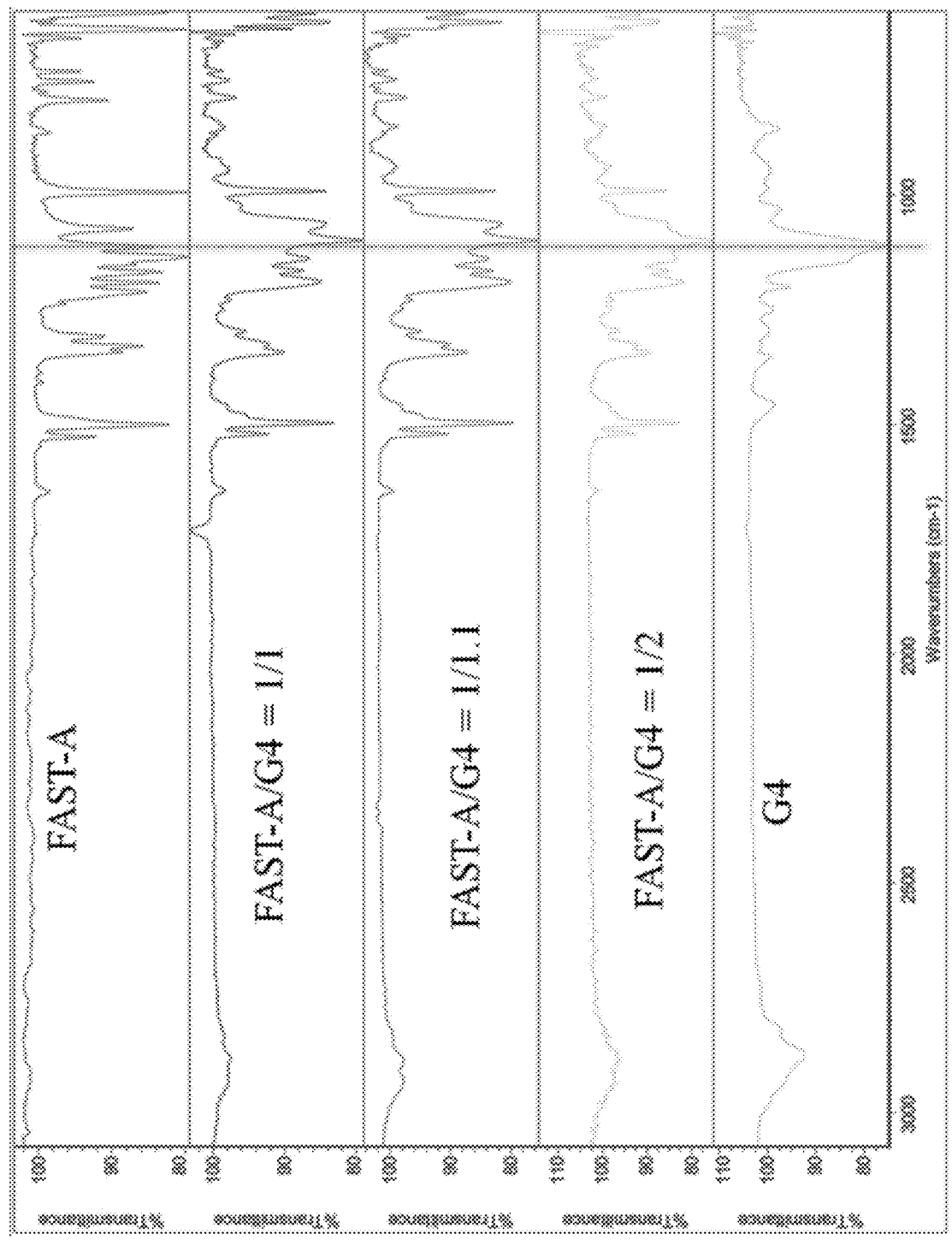

FIG. 8 depicts FTIR spectra for FAST-A, G4, and SILs.

Figure 9:
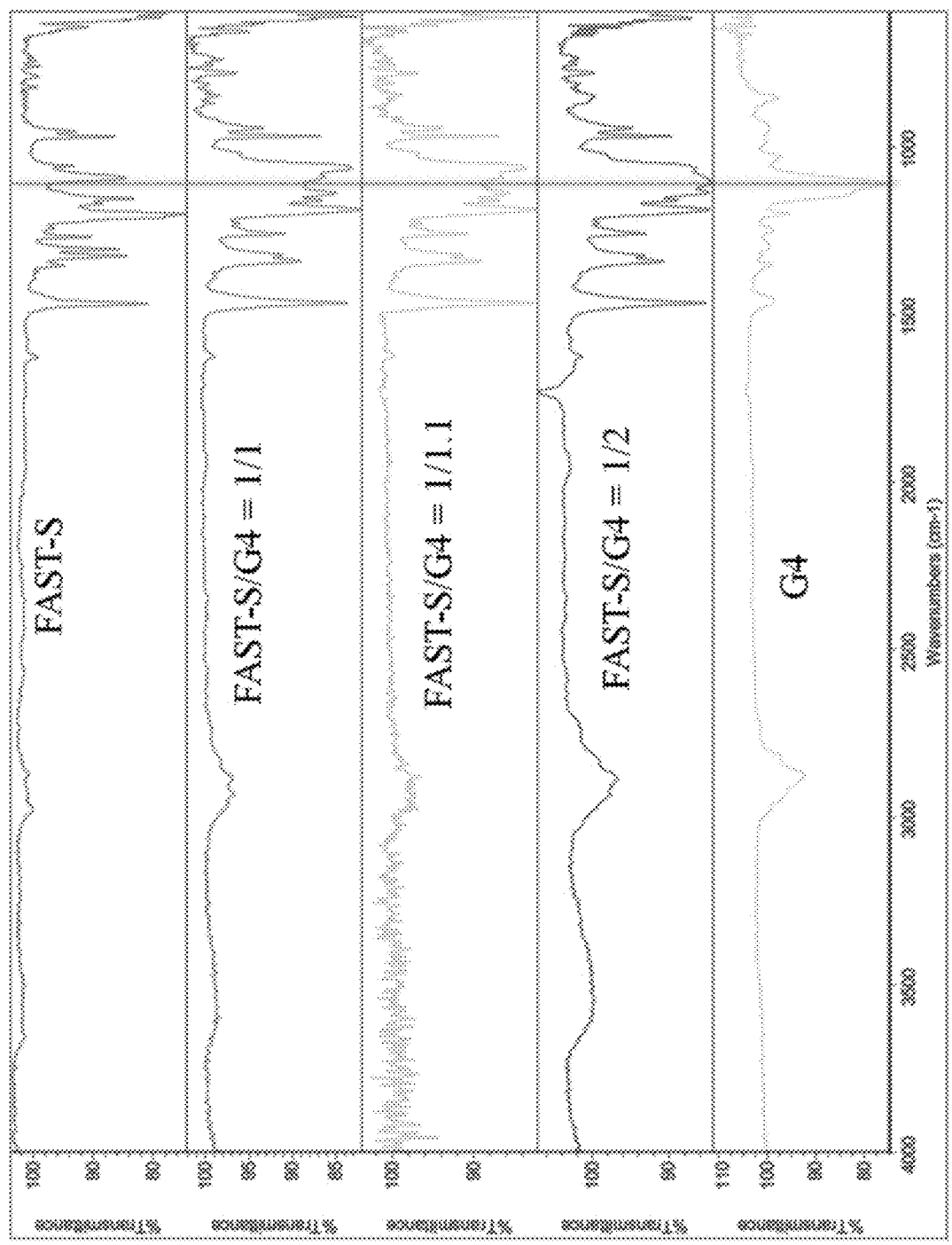

FIG. 9 depicts FTIR spectra for FAST-S, G4, and SILs.

FIG. 10 depicts conductivity of sulfamide neutral polymer+LiTFSI SIL (G4:LiTFSI=1:1). In summary, room temperature conductivity of >10$^{-4}$ (marked with asterisk) observed for polymer+SIL, which is nearly 2 orders of magnitude greater than polymer blended with LiTFSI. Unlike G4:LiTFS=1:1 SIL, which is a liquid, the polymer blend is a honey-like viscoelastic material that does not flow readily, which can be a major improvement in mechanical properties.

FIG. 11 depicts EC stability polymers+SIL (G4:LiTFSI=1:1).

Polymer blended with SIL is significantly more electrochemically stable than the G4:LiTFSI SIL and the polymer alone (data not shown for polymer alone, but it is oxidized at much lower potential).

Therefore, the material is a highly electrochemically stable polymer:SIL composite with RT conductivity>10$^{-4}$.

FIG. 12 depicts conductivity of SIL based on polyanion+G4.

Details of one or more embodiments are set forth in the accompanying drawings and description. Other features, objects, and advantages will be apparent from the description, drawings, and claims. Although a number of embodiments of the invention have been described, it will be understood that various modifications may be made without departing from the spirit and scope of the invention. It should also be understood that the appended drawings are not necessarily to scale, presenting a somewhat simplified representation of various features and basic principles of the invention.

What is claimed:

1. A composition comprising a compound of formula I:

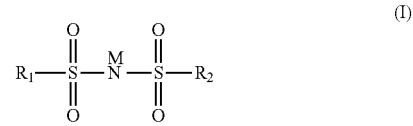

wherein

M is a metal cation;

R$_1$ is alkyl, alkenyl, alkynyl, aryl, heteroaryl, or alkoxy; and

R$_2$ is alkyl, alkenyl, alkynyl, aryl, heteroaryl, or alkoxy, wherein at least one of $R_1$ and $R_2$ is substituted and includes at least one fluorine and wherein the composition is a solvate ionic liquid.

2. The composition of claim 1, wherein M is a lithium ion, a sodium ion, or a potassium ion.

3. The composition of claim 1, wherein $R_1$ is a fluorinated C1-C6 alkyl.

4. The composition of claim 1, wherein $R_2$ is a fluorinated aryl.

5. The composition of claim 1, wherein $R_2$ is a fluorinated aryl optionally substituted with one or more amino group, alkoxy group or alkylthio group.

6. The composition of claim 1, wherein the compound has the formula:

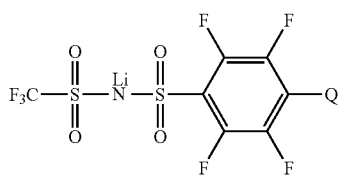

wherein Q is a fluoro, an alkoxy group or alkylthio group.

7. The composition of claim 1, wherein Q is fluoro, C1-C4 alkylthio, C1-C4 alkoxy, or a polyolefin including a thio or oxy moiety.

8. The composition of claim 1, wherein the compound is:

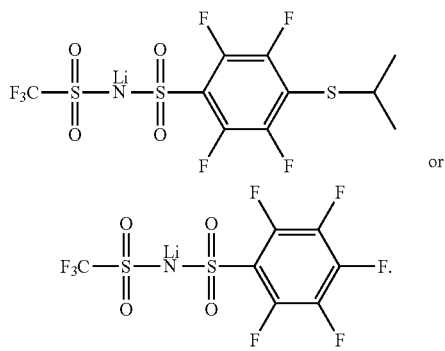

9. A composition comprising a compound comprising a polyolefin including a thio or oxy moiety and having a structure of formula II or formula III

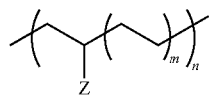
(II)

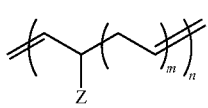
(III)

wherein n is 1-10,000;
each m is 0, 1, 2, or 3; and

Z is

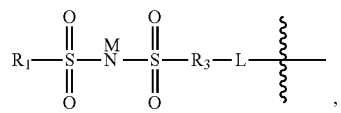

wherein M is a metal cation;
$R_1$ is alkyl, alkenyl, alkynyl, aryl, heteroaryl, or alkoxy;
$R_3$ is alkylene, alkenylene, alkynylene, arylene, heteroarylene, or alkyleneoxy; and
L is O or S; and wherein at least one of $R_1$ and $R_2$ is substituted and includes at least one fluorine and wherein the composition is a solvate ionic liquid.

10. A composition of claim 9, wherein the polyolefin has a structure of formula (IV) or (V):

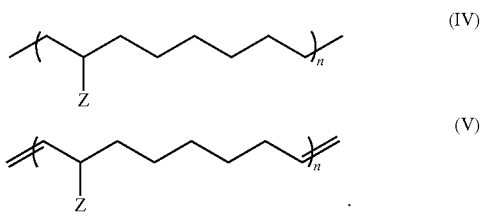

11. The composition of claim 9, wherein M is a lithium ion, a sodium ion, or a potassium ion.

12. The composition of claim 9, wherein $R_1$ is a fluorinated C1-C6 alkyl.

13. The composition of claim 9, wherein $R_3$ is a fluorinated arylene.

14. The composition of claim 9, wherein $R_3$ is a fluorinated arylene optionally substituted with one or more amino group, alkoxy group or alkylthio group.

15. The composition of claim 9, wherein $R_1$ is trifluoromethyl and $R_3$ is fluorinated phenylene.

16. The composition of claim 9, wherein the compound is:

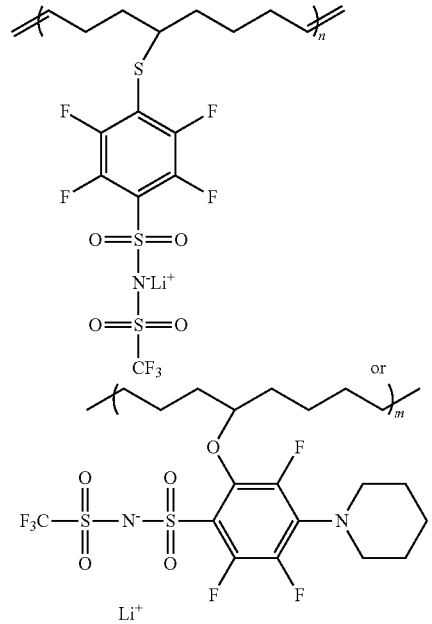

17. A battery including a composition of claim 1.

18. The composition of claim 1, wherein the solvate ionic liquid includes tetraglyme.

19. The composition of claim 9, wherein the solvate ionic liquid includes tetraglyme.

* * * * *